(12) United States Patent
Mou et al.

(10) Patent No.: US 10,962,514 B2
(45) Date of Patent: *Mar. 30, 2021

(54) ACTUATING AND SENSING APPARATUS AND CASING USING THE SAME

(71) Applicant: Microjet Technology Co., Ltd., Hsinchu (TW)

(72) Inventors: Hao-Jan Mou, Hsinchu (TW); Shou-Hung Chen, Hsinchu (TW); Shih-Chang Chen, Hsinchu (TW); Jia-Yu Liao, Hsinchu (TW); Mei-Yen Chen, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 346 days.

This patent is subject to a terminal disclaimer.

(21) Appl. No.: 16/051,978

(22) Filed: Aug. 1, 2018

(65) Prior Publication Data
US 2019/0056367 A1 Feb. 21, 2019

(30) Foreign Application Priority Data

Aug. 21, 2017 (TW) .................................. 106128269

(51) Int. Cl.
*G01N 33/00* (2006.01)
*H05K 5/06* (2006.01)
(Continued)

(52) U.S. Cl.
CPC ....... *G01N 33/0031* (2013.01); *G01N 1/2273* (2013.01); *G01N 1/24* (2013.01); *H05K 5/065* (2013.01)

(58) Field of Classification Search
CPC .. G01N 33/0031; G01N 33/0009; G01N 1/24; G01N 1/2273; H05K 5/065;
(Continued)

(56) References Cited

U.S. PATENT DOCUMENTS

2009/0206699 A1* 8/2009 Osano ................... F04B 43/046
310/317
2014/0377099 A1* 12/2014 Hsueh ..................... F04B 49/22
417/413.2
(Continued)

FOREIGN PATENT DOCUMENTS

| CN | 101515765 A | 8/2009 |
| TW | 201616116 A | 5/2016 |
| TW | 201728904 A | 8/2017 |

*Primary Examiner* — Suman K Nath
(74) *Attorney, Agent, or Firm* — Birch, Stewart, Kolasch & Birch, LLP

(57) ABSTRACT

An actuating and sensing apparatus includes a circuit board, a housing, an actuating device and a sensor. The housing is disposed on the circuit board and includes an entrance opening, an exit opening and a compartment. The compartment is in communication with an external environment of the housing through the entrance opening and the exit opening. The actuating device is disposed within the compartment and closing the exit opening. The sensor is disposed within the compartment and corresponding to the entrance opening. When the actuating device is enabled, a gas within the compartment is guided to the external environment outside the housing, and a pressure gradient is generated in the compartment so as to introduce a gas from the external environment outside the housing into the compartment through the entrance opening to make the gas detected by the sensor.

12 Claims, 10 Drawing Sheets

(51) Int. Cl.
*G01N 1/22* (2006.01)
*G01N 1/24* (2006.01)

(58) Field of Classification Search
CPC ............... F04B 45/047; B81B 3/0021; B81B 2201/036; B81B 2203/0127; B81B 2203/053; F05B 2220/709; H01L 41/0926
See application file for complete search history.

(56) References Cited

U.S. PATENT DOCUMENTS

| | | | |
|---|---|---|---|
| 2016/0054215 A1* | 2/2016 | Williamson | G08B 17/117 73/28.01 |
| 2016/0258896 A1* | 9/2016 | Uesugi | G01N 27/404 |
| 2017/0351221 A1* | 12/2017 | Balti | G01N 33/0039 |

* cited by examiner

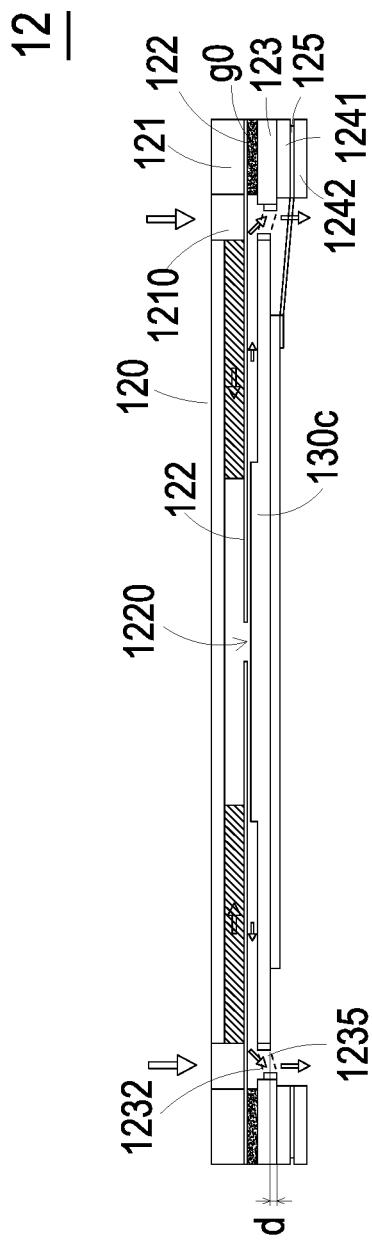
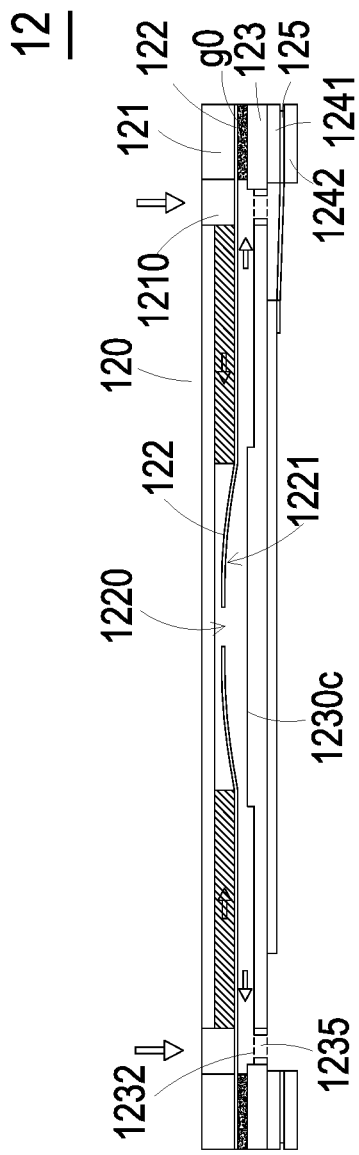

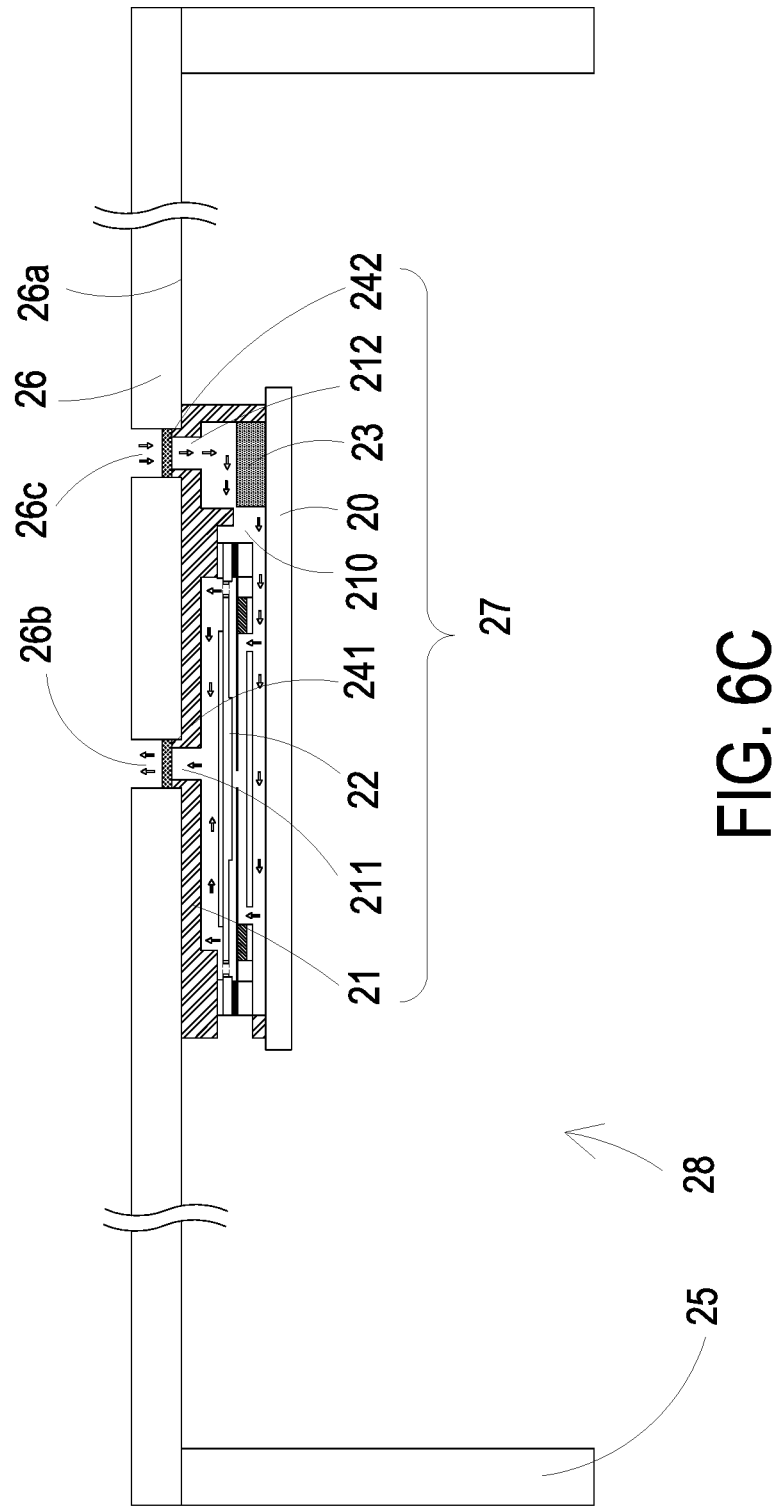

ACTUATING AND SENSING APPARATUS AND CASING USING THE SAME

FIELD OF THE INVENTION

The present disclosure relates to an actuating and sensing apparatus and a casing including the same, and more particularly to an actuating and sensing apparatus and a casing using the same for transmitting gas by an actuating device.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these substances in the environment can cause human health problems or can even harm the life. Therefore, it has become an important issue for every country to develop and implement environmental air quality monitoring technology.

However, the conventional environmental gas detector (e.g., the air cleaner) is bulky in volume and inconvenient to carry around. That is, it is difficult for the user to acquire the information of the ambient gas. Consequently, the user may be exposed to the environment containing the harmful gas. Therefore, it is important to acquire the information of the ambient gas everywhere and at any time.

Moreover, since the conventional environmental gas detector is not waterproof and dustproof, some problems occur. If moisture or liquid is introduced into the environmental gas detector during the process of transferring the gas, the outputted gas contains moisture. In case that the electronic component for sensing the gas is contacted with the gas, the electronic component is possibly damped, rusted or even damaged. Moreover, the conventional environmental gas detector is not dustproof. If dust is introduced into the environmental gas detector during the process of transferring the gas, the components are possibly damaged and the gas transportation efficiency is reduced. Therefore, it is important to achieving the waterproof and dustproof efficacy of the environmental gas detector.

For solving the above drawbacks, it is important to provide a miniature, silent, waterproof and dustproof actuating and sensing apparatus.

SUMMARY OF THE INVENTION

An object of the present disclosure provides an actuating and sensing apparatus. When a piezoelectric actuator of the actuating and sensing apparatus is activated, a pressure gradient is generated in the fluid channel to facilitate the gas to flow at a high speed. Moreover, since there is an impedance difference between the feeding direction and the exiting direction of the fluid channel, the gas can be transmitted from the inlet side to the outlet side. Consequently, the volume of the equipment or machine with the conventional environmental gas detector and the generated noise will be reduced.

Another object of the present disclosure provides an actuating and sensing apparatus having waterproof and dustproof efficacy. The actuating and sensing apparatus is equipped with a protective film to filter the moisture and the dust. Since the moisture and the dust are not introduced into the inner portion of the actuating and sensing apparatus, the components are not damaged by the moisture and the dust and the gas transportation efficiency is enhanced.

A further object of the present disclosure provides a casing of an electronic device suitable for an actuating and sensing apparatus. Since the actuating and sensing apparatus is miniature and silent, it could be installed in the casing of a smart phone thereby achieving the portable purpose and the air quality can be immediately monitored everywhere and at any time.

In accordance with an aspect of the present disclosure, an actuating and sensing apparatus is provided. The actuating and sensing apparatus includes a circuit board, a housing, an actuating device and a sensor. The housing is disposed on the circuit board and includes an entrance opening, an exit opening and a compartment. The compartment is in communication with an external environment outside the housing through the entrance opening and the exit opening. The actuating device is disposed within the compartment and closing the exit opening. The sensor is disposed within the compartment and corresponding to the entrance opening. When the actuating device is enabled, a gas within the compartment is guided to the external environment outside the housing, and a pressure gradient is generated in the compartment so as to introduce the gas from the external environment outside the housing into the compartment through the entrance opening to make the gas monitored by the sensor.

In accordance with another aspect of the present disclosure, a casing for using in an electronic device is provided. The casing includes an actuating and sensing apparatus, a plate and a lateral wall. The actuating and sensing apparatus includes a circuit board, a housing, an actuating device and a sensor. The housing is disposed on the circuit board and comprises an entrance opening, an exit opening and a compartment. The compartment is in communication with an external environment outside the housing through the entrance opening and the exit opening. The actuating device is disposed within the compartment and closes the exit opening. The sensor is disposed within the compartment and corresponding to the entrance opening. The plate includes a bottom surface, a first opening and a second opening. The housing of the actuating and sensing apparatus is attached on the bottom surface. The entrance opening is aligned and in communication with the second opening. The exit opening is aligned and in communication with the first opening. The lateral wall is connected to the plate. When the actuating device of the actuating and sensing apparatus is enabled, a gas within the compartment is guided to an external environment outside the casing through the exit opening and the first opening, and a pressure gradient is generated in the compartment so as to introduce the gas from the external environment outside the casing into the compartment through the second opening and the entrance opening to make the gas monitored by the sensor.

The above contents of the present disclosure will become more readily apparent to those ordinarily skilled in the art after reviewing the following detailed description and accompanying drawings, in which:

BRIEF DESCRIPTION OF THE DRAWINGS

FIGS. 5A to 5E schematically illustrate the actions of the actuating device of FIG. 3A;

FIG. 6C is a schematic cross-sectional view illustrating the the actuating and sensing apparatus and the casing of the electronic device of FIG. 6A and taken along the line BB.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
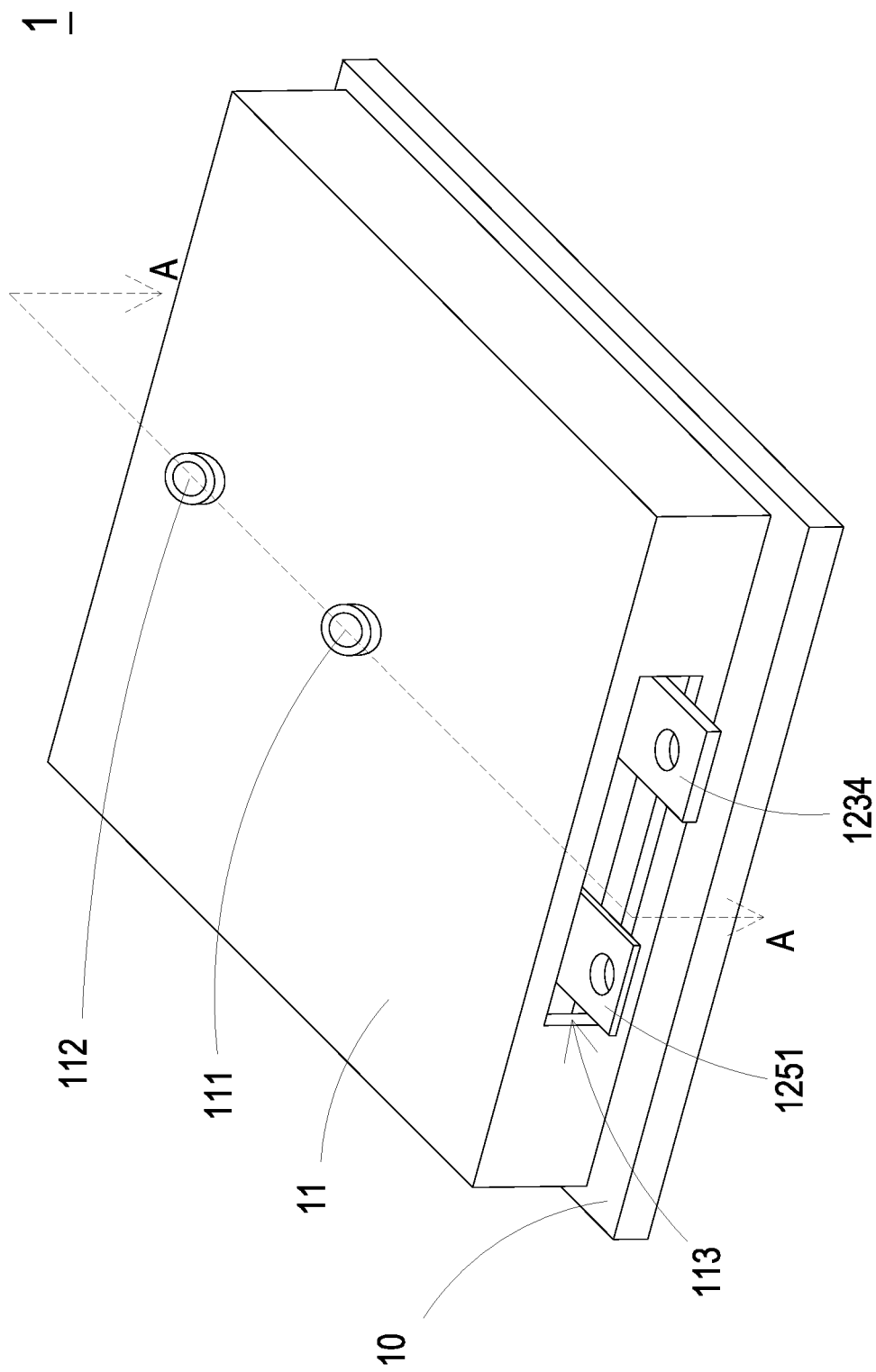
FIG. 1 is a schematic perspective view illustrating the outer appearance of an actuating and sensing apparatus according to an embodiment of the present disclosure and taken along a front side.
Figure 2:
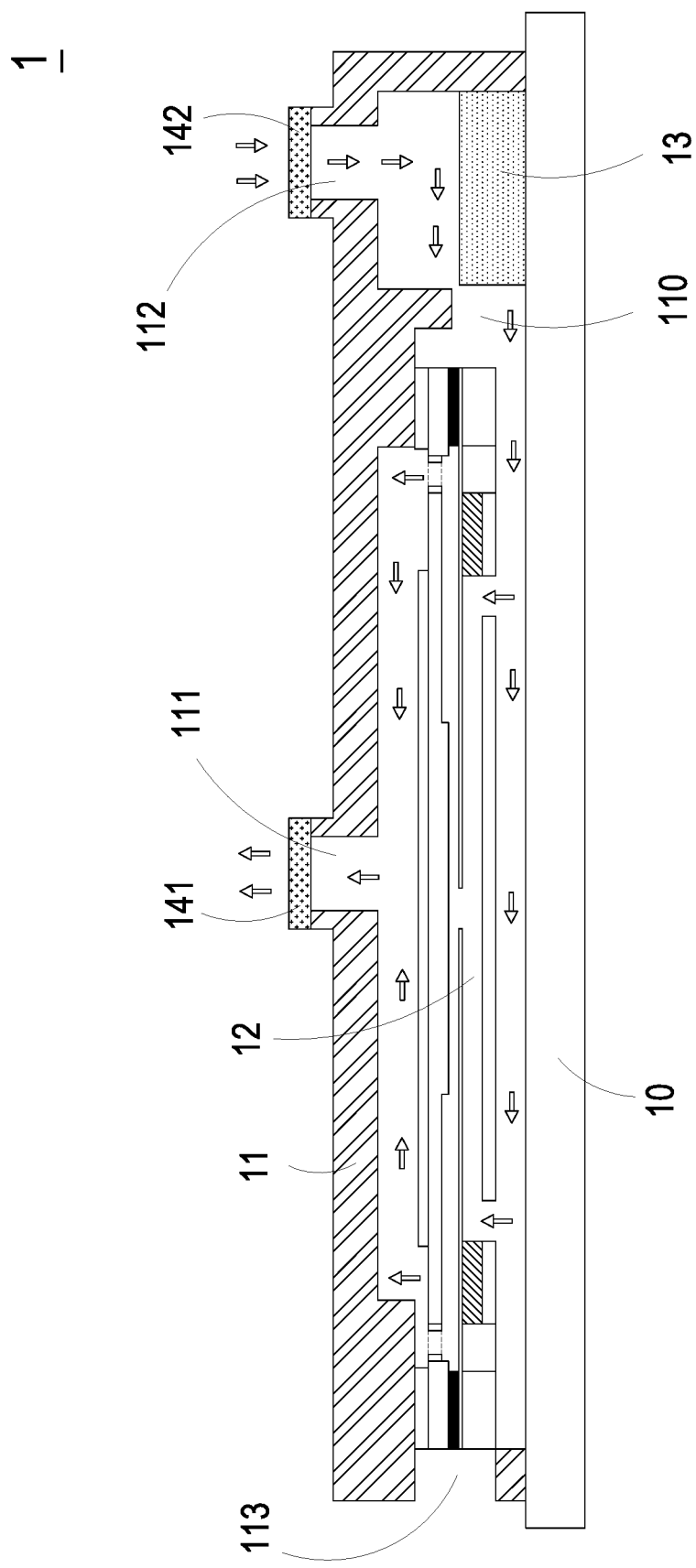
FIG. 2 is a schematic cross-sectional view illustrating the actuating and sensing apparatus of FIG. 1 and taken along the line AA.

Please refer to FIGS. 1 and 2. The present discourse provides an actuating and sensing apparatus 1 including at least one circuit board 10, at least one housing 11, at least one at entrance opening 112, at least one exit opening 111, at least one compartment 110, at least one actuating device 12 and at least one sensor 13. The number of the circuit board 10, the housing 11, the entrance opening 112, the exit opening 111, the compartment 110, the actuating device 12 and the sensor 13 is exemplified by one for each in the following embodiments but not limited thereto. It is noted that each of the circuit board 10, the housing 11, the entrance opening 112, the exit opening 111, the compartment 110, the actuating device 12 and the sensor 13 can also be provided in plural numbers.

FIG. 1 is a schematic perspective view illustrating the outer appearance of an actuating and sensing apparatus according to an embodiment of the present disclosure and taken along a front side. FIG. 2 is a schematic cross-sectional view illustrating the actuating and sensing apparatus of FIG. 1 and taken along the line AA. The actuating and sensing apparatus 1 of the present disclosure is capable of monitoring the quality of the ambient gas while achieving the waterproof, dustproof and silent efficacy. The actuating and sensing apparatus 1 could be used in any portable electronic device. For example, the portable electronic devices may be a notebook computer, a smart phone, a smart watch, a tablet computer or any other appropriate portable electronic device. As shown in FIG. 1 and FIG. 2, in this embodiment, the actuating and sensing apparatus 1 includes a circuit board 10, a housing 11, an actuating device 12 and a sensor 13. The circuit board 10 is a platform for integrating the housing 11, the actuating device 12 and the sensor 13. The circuit board 11 could be but not limited to a printed circuit board (PCB) for installing the housing 11, the actuating device 12 and the sensor 13, and providing a driving power to the actuating device 12 and the sensor 13, thereby enabling the actuating device 12 and the sensor 13. In an embodiment, the housing 11 covers upon the circuit board 10. The housing includes a compartment 110, an exit opening 111, an entrance opening 112 and a window 113. The entrance opening 112 and the exit opening 111 are disposed on an external surface of the housing 11, so that the compartment 110 could be in communication with an external environment outside the housing 11 through the entrance opening 112 and the exit opening 113. The window 113 is disposed on a lateral wall of the housing 11, and the conducting pins 1234 and 1251 of the actuating device 12 could be disposed therethrough (as shown in FIG. 1). In this embodiment, the housing 11 is a shell structure made of thermosetting plastic material, but no limited thereto.

Please refer to FIGS. 1 and 2 again. The actuating device 12 is disposed within the compartment 110 of the housing 11 and closes the exit opening 111. The actuating device 12 is used for guiding the gas within the compartment 110 to the external environment of the housing 11 through the exit opening 111, so that a pressure gradient is generated in the compartment 110. The sensor 13 is disposed within the compartment 110 of the housing 11. The sensor 13 is aligned with and corresponding to the entrance opening 112 for detecting the concentrations and contents of the gases in the air. When the actuating device 12 is enabled, the gas in the compartment 110 is guided to the external environment outside the housing 11 through the exit opening 111, and thus a pressure gradient is generated in the compartment 110 so as to introduce the gas from the external environment outside the housing 11 into the compartment 110 through the entrance opening 112 to make the gas monitored by the sensor 13. The flow of the gas is driven by the pressure difference between the compartment 110 and the atmosphere. Consequently, the information about the result of monitoring the ambient gas is acquired. As the actuating device 12 is continuously enabled, the gas is continuously guided into the compartment 110, and the gas flows through the entrance opening 112, the compartment 110 and the exit opening 111 in sequence. Since the concentrations and contents of the gases in the compartment 110 are continuously monitored by the sensor 13, the information about the result of monitoring the ambient gas can be acquired in real time. In this embodiment, the speed of the gas circulation is accelerated by the actuator 12, so that the sensor 13 can monitor the immediate ambient gas information. When the ambient gas is detected to contain toxic gas or dangerous gas, the user could be warned that the concentration or content of the harmful gas in the environment is too high. After realizing the harmful level of the ambient gas, the user can escape quickly or take protective measures. Consequently, the possibility of causing the user's coma, poisoning the user or resulting in gas explosion will be largely reduced.

In this embodiment, the actuating and sensing apparatus 1 includes the length of 19.7 mm, the width of 15.8 mm and the height of 3.4 mm. The circuit board 10 of the actuating and sensing apparatus 1 includes the length of 19.7 mm, the width of 15.8 mm and the height of 0.8 mm. The housing 11 of the actuating and sensing apparatus 1 includes the length of 17.8 mm, the width of 14.8 mm and the height of 2.6 mm, but not limited thereto. Since the overall volume and thickness of the actuating and sensing apparatus 1 are reduced, the actuating and sensing apparatus 1 can be applied to the miniature device or the portable electronic device. By using the portable electronic device of the present disclosure, the information about the ambient gas can be immediately monitored everywhere and at any time.

In this embodiment, an example of the sensor 13 includes an oxygen sensor, a carbon monoxide sensor, a carbon dioxide sensor, a temperature sensor, an ozone sensor, a sulfur dioxide sensor, a nitrogen dioxide sensor, a volatile organic compound sensor (e.g., a sensor for measuring formaldehyde or ammonia gas), or combinations thereof. In some embodiments, the sensor 13 includes a fine suspended particulate sensor or a suspended particulate sensor.

Please refer to FIG. 2 again. The actuating and sensing apparatus 1 further includes a first protective film 141 and a second protective film 142. The first protective film 141 and the second protective film 142 are respectively close the exit opening 111 and the entrance opening 112. The first protective film 141 and the second protective film 142 are waterproof and dustproof film structures. Moreover, the gas is allowed to pass through the first protective film 141 and the second protective film 142. Since the first protective film 141 and the second protective film 142 are waterproof and dustproof, the moisture and the dust are prevented from entering the compartment 110 through the entrance opening 112 and the exit opening 111, and the actuating device 12 and the sensor 13 within the compartment 110 are not rusted or damaged. In this embodiment, the first protective film 141 and the second protective film 142 comply with the Rating IP64 of International Protection Marking (IEC 60529), i.e., Dust protection level 6 (Complete protection, No ingress of dust) and Water protection level 4 (Protection against Splashing of water: Water splashing against the enclosure from any direction shall have no harmful effect). In another embodiment, the first protective film 141 and the second protective film 142 comply with the Rating IP68 of International Protection Marking (IEC 60529), i.e., Dust protection level 6 and Water protection level 8 (Continuous immersion in water that it produces no harmful effects).

In an embodiment, the actuating and sensing apparatus 1 further includes a battery (not shown). The battery is disposed within the housing 11 and electrically connected to the circuit board 10. That is, the battery of the actuating and sensing apparatus 1 is directly used as the power source to generate the driving power. The driving power is transmitted to the actuating device 12 and the sensor 13. In another embodiment, the circuit board 10 of the actuating and sensing apparatus 1 is connected to an external power source (not shown), such as a charger, a rechargeable battery, or a wireless rechargeable component, which is not restricted.

In this embodiment, the actuating device 12 is an air pump with a resonant piezoelectric actuator. In some embodiments, the actuating device 12 is a driving device capable of driving a desired system in response to a control signal. An example of the actuating device 12 includes but is not limited to an electric actuating device, a magnetic actuating device, a thermal actuating device, a piezoelectric actuating device, and a fluid actuating device. For example, the electric actuating device is an electric actuating device of a DC motor, an AC motor or a step motor, the magnetic actuating device is an magnetic actuating device of a magnetic coil motor, the thermal actuating device is a thermal actuating device of a heat pump, the piezoelectric actuating device is a piezoelectric actuating device of a piezoelectric pump, and the fluid actuating device is a fluid actuating device of an air pump or a liquid pump.

Figure 3A:
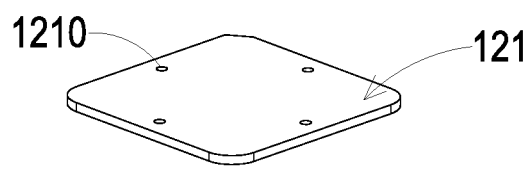
FIG. 3A is a schematic exploded view illustrating an actuating device of the actuating and sensing apparatus according to the embodiment of the present disclosure and taken along a front side.
Figure 3A:
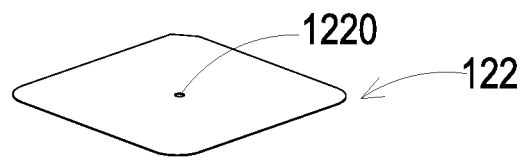
Figure 3A:
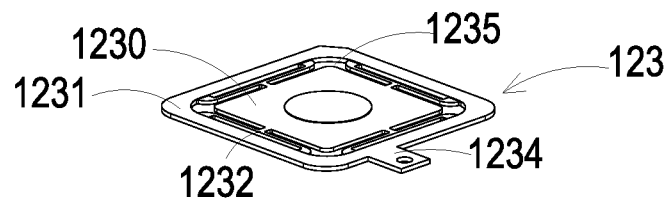
Figure 3A:
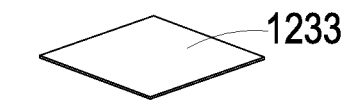
Figure 3A:
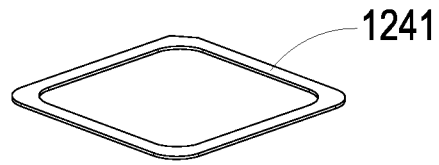
Figure 3A:
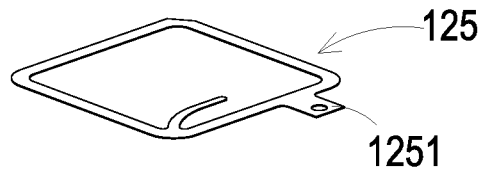
Figure 3A:
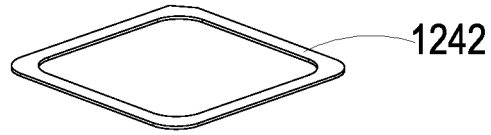
Figure 3B:
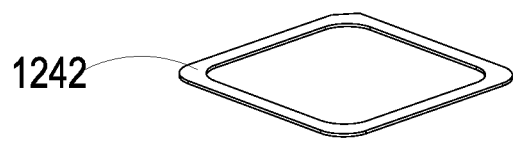
FIG. 3B is a schematic exploded view illustrating the actuating device of FIG. 3A and taken along a rear side.
Figure 3B:
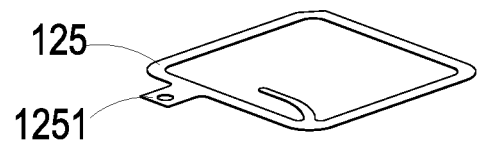
Figure 3B:
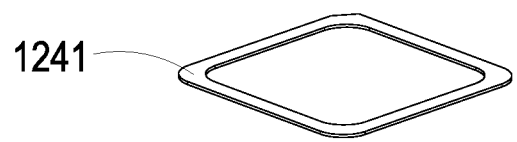
Figure 3B:
Figure 3B:
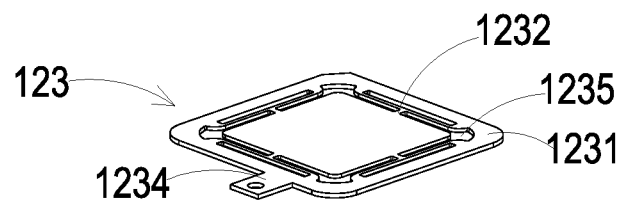
Figure 3B:
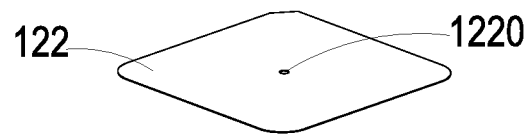
Figure 3B:
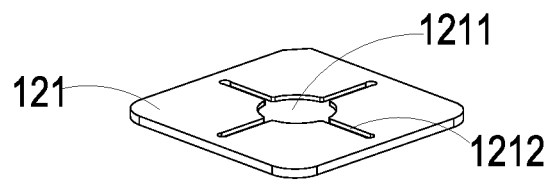

Please refer to FIGS. 3A and 3B. FIG. 3A is a schematic exploded view illustrating the actuating device according to an embodiment of the present disclosure, and FIG. 3B is a schematic exploded view illustrating the actuating device of FIG. 3A and taken along another viewpoint. In this embodiment, the actuating device 12 includes a gas inlet plate 121, a resonance plate 122, a piezoelectric actuator 123, a first insulation plate 1241, a conducting plate 125 and a second insulation plate 1242. The gas inlet plate 121, the resonance plate 122, the piezoelectric actuator 123, the first insulation plate 1241, the conducting plate 125 and the second insulation plate 1242 are stacked on each other sequentially to be assembled together as the actuating device 12. In this embodiment, the piezoelectric actuator 123 is assembled from a suspension plate 1230 and a piezoelectric ceramic plate 1233 and is disposed spatially corresponding to the resonance plate 122. The air is fed from at least one inlet 1210 of the gas inlet plate 121 into the actuating device 12 and passes through plural pressure chambers by enabling the piezoelectric actuator 123, so as to transfer an amount of gas downwardly in a process for gas transfer.

Please refer to FIGS. 3A and 3B again. FIG. 3A is a schematic exploded view illustrating the actuating device of the actuating and sensing apparatus according to the embodiment of the present disclosure and taken along a front side. FIG. 3B is a schematic exploded view illustrating the actuating device of FIG. 3A and taken along a rear side. As shown in FIG. 3A, the actuating device 12 includes the gas inlet plate 121, and the gas inlet plate 121 includes the at least one inlet 1210. In this embodiment, the gas inlet plate 121 includes four inlets 1210. It is noted that the number of the at least one inlet 1210 is not restricted. In response to the action of the atmospheric pressure, the gas can be introduced into the actuating device 12 through the at least one inlet 1210. As shown in FIG. 3B, a central cavity 1211 and at least one convergence channel 1212 are formed in a bottom surface of the gas inlet plate 121. The at least one convergence channel 1212 is aligned with the at least one inlet 1210. In an embodiment, the gas inlet plate 121 has four convergence channels 1212 corresponding to the four inlets 1210. After the gas is introduced into the at least one convergence channel 1212 through the at least one inlet 1211, the gas is guided to the central cavity 1211 and transferred downwardly. In this embodiment, the at least one inlet 1210, the at least one convergence channel 1212 and the central cavity 1211 of the gas inlet plate 121 are integrally formed from a single structure. The central cavity 1211 is a convergence chamber for temporarily storing the gas. In some embodiments, the gas inlet plate 121 may be for example, made of stainless steel. In other embodiments, the depth of the convergence chamber defined by the central cavity 1211 may be equal to the depth of the at least one convergence channel 1212.

In this embodiment, the resonance plate 122 is made of a flexible material. The resonance plate 122 has a central aperture 1220 aligned with the central cavity 1211 of the bottom surface of the gas inlet plate 121 which allows the gas to be transferred therethrough. In other embodiments, the resonance plate 122 may be, for example, made of copper.

Figure 4A:
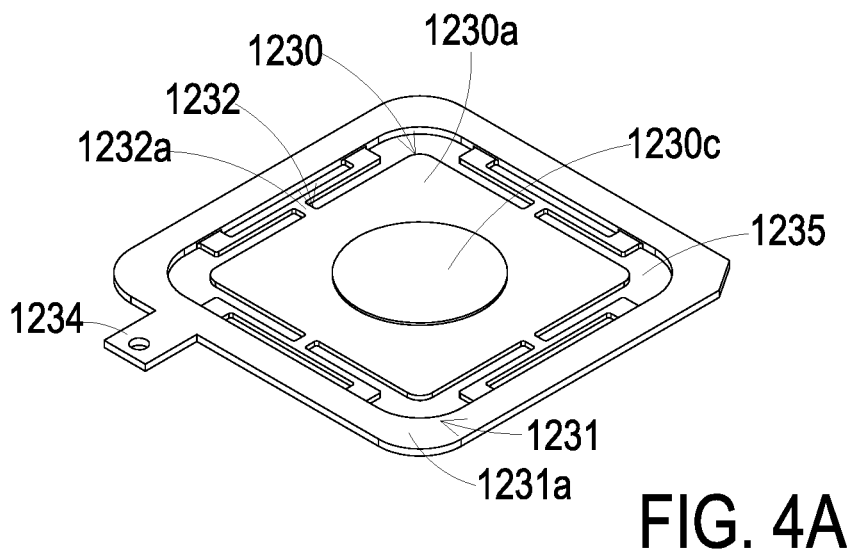
FIG. 4A is a schematic perspective view illustrating the piezoelectric actuator of the actuating device of FIG. 3A and taken along the front side.
Figure 4B:
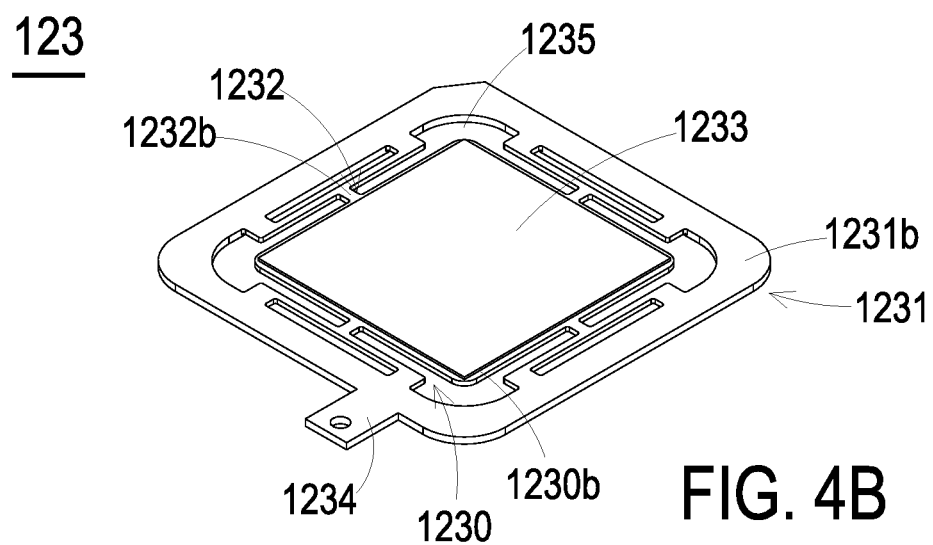
FIG. 4B is a schematic perspective view illustrating the piezoelectric actuator of the actuating device of FIG. 3A and taken along the rear side.
Figure 4C:
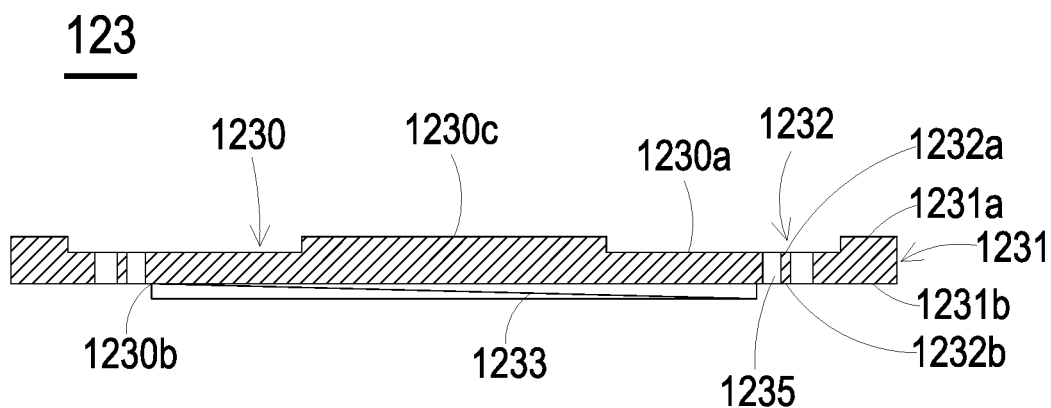
FIG. 4C is a schematic cross-sectional view illustrating the piezoelectric actuator of the actuating device of FIG. 3A.

Please refer to FIGS. 4A to 4C. FIG. 4A is a schematic perspective view illustrating the piezoelectric actuator of the actuating device of FIG. 3A and taken along the front side. FIG. 4B is a schematic perspective view illustrating the piezoelectric actuator of the actuating device of FIG. 3A and taken along the rear side. FIG. 4C is a schematic cross-sectional view illustrating the piezoelectric actuator of the actuating device of FIG. 3A. In this embodiment, the piezoelectric actuator 123 includes a suspension plate 1230, an outer frame 1231, plural brackets 1232 and a piezoelectric ceramic plate 1233. The piezoelectric ceramic plate 1233 is attached on a bottom surface 1230b of the suspension plate 1230. The plural brackets 1232 are connected between the suspension plate 1230 and the outer frame 1231, while the two ends of the brackets 1232 are connected to the outer frame 1231 and the suspension plate 1230 respectively that the brackets 1232 can elastically support the suspension plate 1230. At least one vacant space 1235 is formed between the bracket 1232, the suspension plate 1230 and the outer frame 1231 for allowing the gas to flow through. The type of the suspension plate 1230 and the outer frame 1231 and the type and the number of the at least one bracket 1232 may be varied according to the practical requirements. Moreover, a conducting pin 1234 is protruded outwardly from the outer frame 1231 so as to be electrically connected to an external circuit (not shown).

In this embodiment, the suspension plate 1230 has a bulge 1230c that makes the suspension plate 1230 a stepped structure. The bulge 1230c is formed on a top surface of 1230a of the suspension plate 1230. The bulge 1230c may be a circular convex structure. Please refer to FIGS. 4A, 4B and 4C. A top surface of the bulge 1230c of the suspension plate 1230 is coplanar with a top surface 1231a of the outer frame 1231, and the top surface 1230a of the suspension plate 1230 is coplanar with a top surface 1232a of the bracket 1232. Moreover, there is a specific depth from the bulge 1230c of the suspension plate 1230 (or the top surface 1231a of the outer frame 1231) to the top surface 1230a of the suspension plate 1230 (or the top surface 1232a of the bracket 1232). Please refer to FIGS. 4B and 4C. A bottom surface 1230b of the suspension plate 1230, the bottom surface 1231b of the outer frame 1231 and a bottom surface 1232b of the bracket 1232 are coplanar with each other. The piezoelectric ceramic plate 1233 is attached on the bottom surface 1230b of the suspension plate 1230. In some embodiments, the suspension plate 1230, the brackets 1232 and the outer frame 1231 may be integrally formed from a metal plate (e.g., a stainless steel plate).

Please refer to FIGS. 3A and 3B again. In this embodiment, the first insulation plate 1241, the conducting plate 125 and the second insulation plate 1242 of the actuating device 12 are stacked on each other sequentially and located under the piezoelectric actuator 123. The profiles of the first insulation plate 1241, the conducting plate 125 and the second insulation plate 1242 substantially match the profile of the outer frame 1231 of the piezoelectric actuator 123. In some embodiments, the first insulation plate 1241 and the second insulation plate 1242 may be made of an insulating material (e.g. a plastic material) for providing insulating efficacy. In other embodiments, the conducting plate 125 may be made of an electrically conductive material (e.g. a metallic material) for providing electrically conducting efficacy. In this embodiment, the conducting plate 125 may have a conducting pin 1251 disposed thereon so as to be electrically connected to an external circuit (not shown).

Figure 5A:
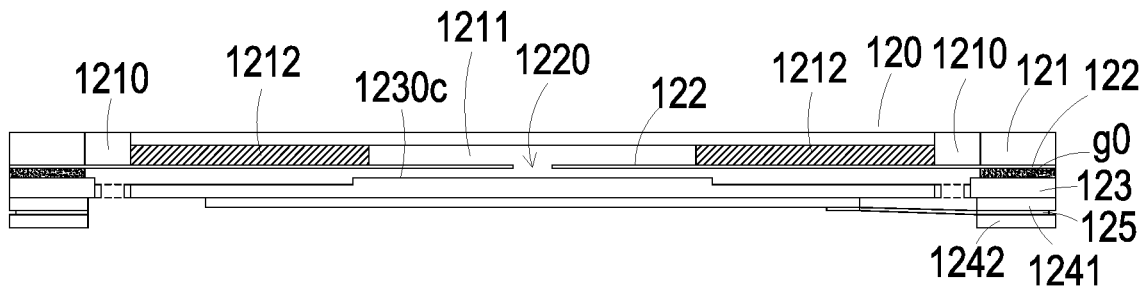

Please refer to FIGS. 3A and 3B and FIGS. 5A to 5E. FIGS. 5A to 5E schematically illustrate the actions of the actuating device of FIG. 3A. As shown in FIG. 5A, the gas inlet plate 121, the resonance plate 122, the piezoelectric actuator 123, the first insulation plate 1241, the conducting plate 125 and the second insulation plate 1242 are stacked on each other sequentially. Moreover, there is a gap g0 between the resonance plate 122 and the piezoelectric actuator 123. In this embodiment, the gap g0 between the resonance plate 122 and the outer frame 1231 of the piezoelectric actuator 123 may be filled with a filler (e.g. a conductive adhesive) so that a depth from the resonance plate 122 to the bulge 1230c of the suspension plate 1230 of the piezoelectric actuator 123 can be maintained. The gap g0 ensures the proper distance between the resonance plate 122 and the bulge 1230c of the suspension plate 1230 of the piezoelectric actuator 123, so that the gas can be transferred quickly, the contact interference is reduced and the generated noise is largely reduced. In some embodiments, alternatively, the height of the outer frame 1231 of the piezoelectric actuator 123 is increased, so that the gap is formed between the resonance plate 122 and the piezoelectric actuator 123.

Please refer to FIGS. 5A to 5E again. After the gas inlet plate 121, the resonance plate 122 and the piezoelectric actuator 123 are combined together, the convergence chamber for converging the gas is further defined by the central aperture 1220 of the resonance plate 122 and the central cavity 1211 of the gas inlet plate 121 collaboratively, and a first chamber 1221 is formed between the resonance plate 122 and the piezoelectric actuator 123 for temporarily storing the gas. Through the central aperture 1220 of the resonance plate 122, the first chamber 1221 is in communication with the convergence chamber formed within the central cavity 1211 of the gas inlet plate 121. The peripheral regions of the first chamber 1221 are in communication with the compartment 110 of the housing 11 (see FIG. 2) through the vacant space 1235 between the brackets 1232 of the piezoelectric actuator 123.

Figure 5B:
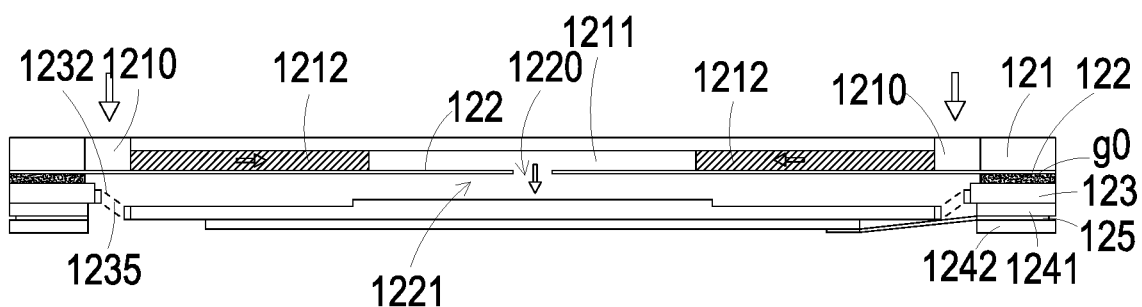
Figure 5C:
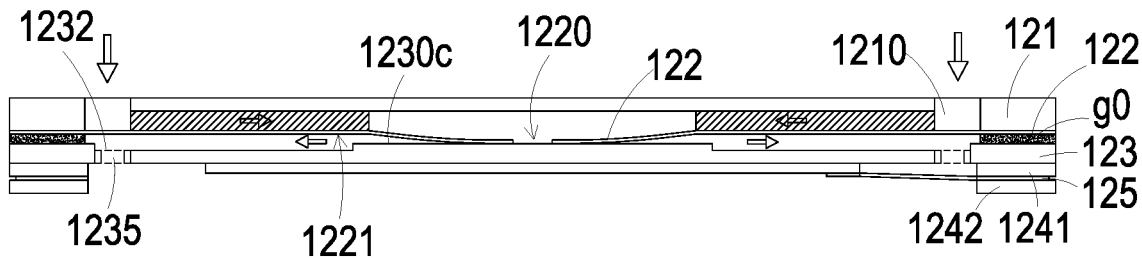

In this embodiment, when the actuating device 12 is enabled, the piezoelectric actuator 123 vibrates along a vertical direction in a reciprocating manner by using the bracket 1232 as a fulcrum. As shown in FIG. 5B, the piezoelectric actuator 123 vibrates downwardly in response to the applied voltage. In that case, the gas is inhaled and filtered by the first protective film 141, as shown in FIG. 2. After the moisture and dust in the gas are filtered out by the first protective film 141, the gas is continuously fed into the at least one inlet 1210 of the convergence plate 12 through the entrance opening 112. Then, the gas is converged to the central cavity 1211 of the gas inlet plate 121 through the at least one convergence channel 1212, and transferred downwardly to the first chamber 1221 through the central aperture 1220 of the resonance plate 122. Driven by the vibration of the piezoelectric actuator 123, the resonance plate 122 is in resonance with the piezoelectric actuator 123, and thus the resonance plate 122 vibrates along the vertical direction in the reciprocating manner. As shown in FIG. 5C, the resonance plate 122 vibrates downwardly, so as to contact and attach on the bulge 1230c of the suspension plate 1230 of the piezoelectric actuator 123. Owing to the deformation of the resonance plate 122 described above, a middle communication space of the first chamber 1221 is closed, and the volume of the first chamber 1221 is compressed. Under this circumstance, the pressure gradient occurs to push the gas in the first chamber 1221 toward peripheral regions of the first chamber 1221, and flowing downwardly through the vacant space 1235 of the piezoelectric actuator 123. As shown in FIG. 5D, the resonance plate 122 returns to its original position when the piezoelectric actuator 123 deforms upwardly during the vibration. Consequently, the volume of the first chamber 1221 is continuously compressed. Since the piezoelectric actuator 123 is ascended for a displacement d, the gas is continuously pushed toward peripheral regions of the first chamber 1221. Meanwhile, the gas is continuously fed into the at least one inlet 1210 of the gas inlet plate 121 and transferred to the convergence chamber formed within the central cavity 1211, and thus filtered by the first protective film 141 continuously. Then, as shown in FIG. 5E, influenced by the upward motion of the piezoelectric actuator 123, the resonance plate 122 moves upwardly. Under this circumstance, the gas in the central cavity 1211 is transferred to the first chamber 1221 through the central aperture 1220 of the resonance plate 122, then the gas is transferred downwardly through the vacant space 1235 of the piezoelectric actuator 123, and finally the gas is discharged from the actuating device 12. Consequently, a pressure gradient is generated in the fluid channels of the actuating device 12 to facilitate the gas to flow at a high speed. Moreover, since there is an impedance difference between the feeding direction and the exiting direction, the gas can be transmitted from the inlet side to the outlet side. Even if a gas pressure exists at the outlet side, the actuating device 12 still has the capability of pushing the gas to the outlet side while achieving the silent efficacy. In some embodiments, the vibration frequency of the resonance plate 122 along the vertical direction in the reciprocating manner is identical to the vibration frequency of the piezoelectric actuator 123. That is, the resonance plate 122 and the piezoelectric actuator 123 are synchronously vibrated along the upward direction or the downward direction. It is noted that numerous modifications and alterations of the actions of the actuating device 12 may be made while retaining the teachings of the invention.

Figure 6A:
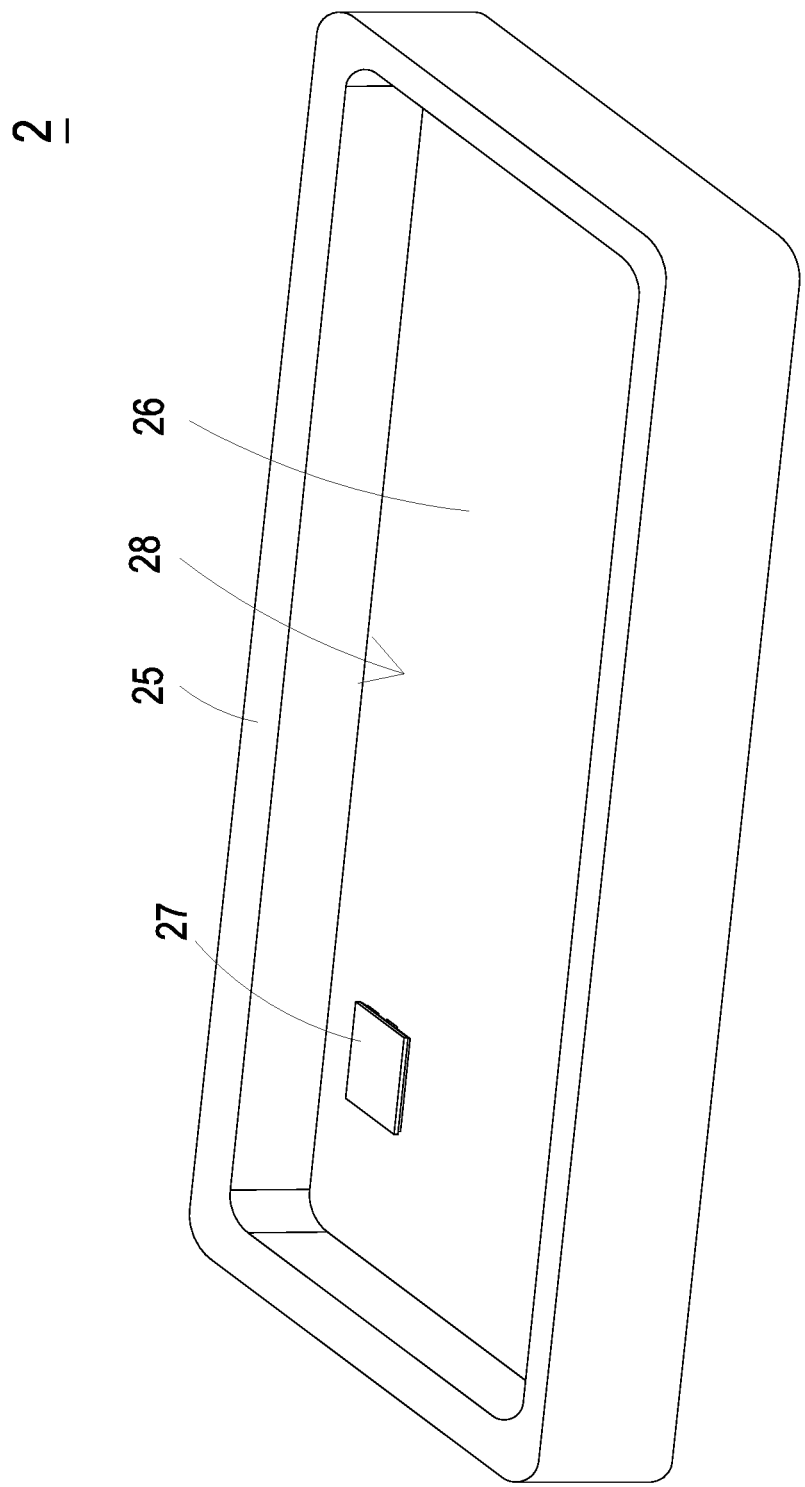
FIG. 6A is a schematic perspective view illustrating the outer appearance of the actuating and sensing apparatus and a casing of an electronic device according to the embodiment of the present disclosure and taken along a front side.
Figure 6B:
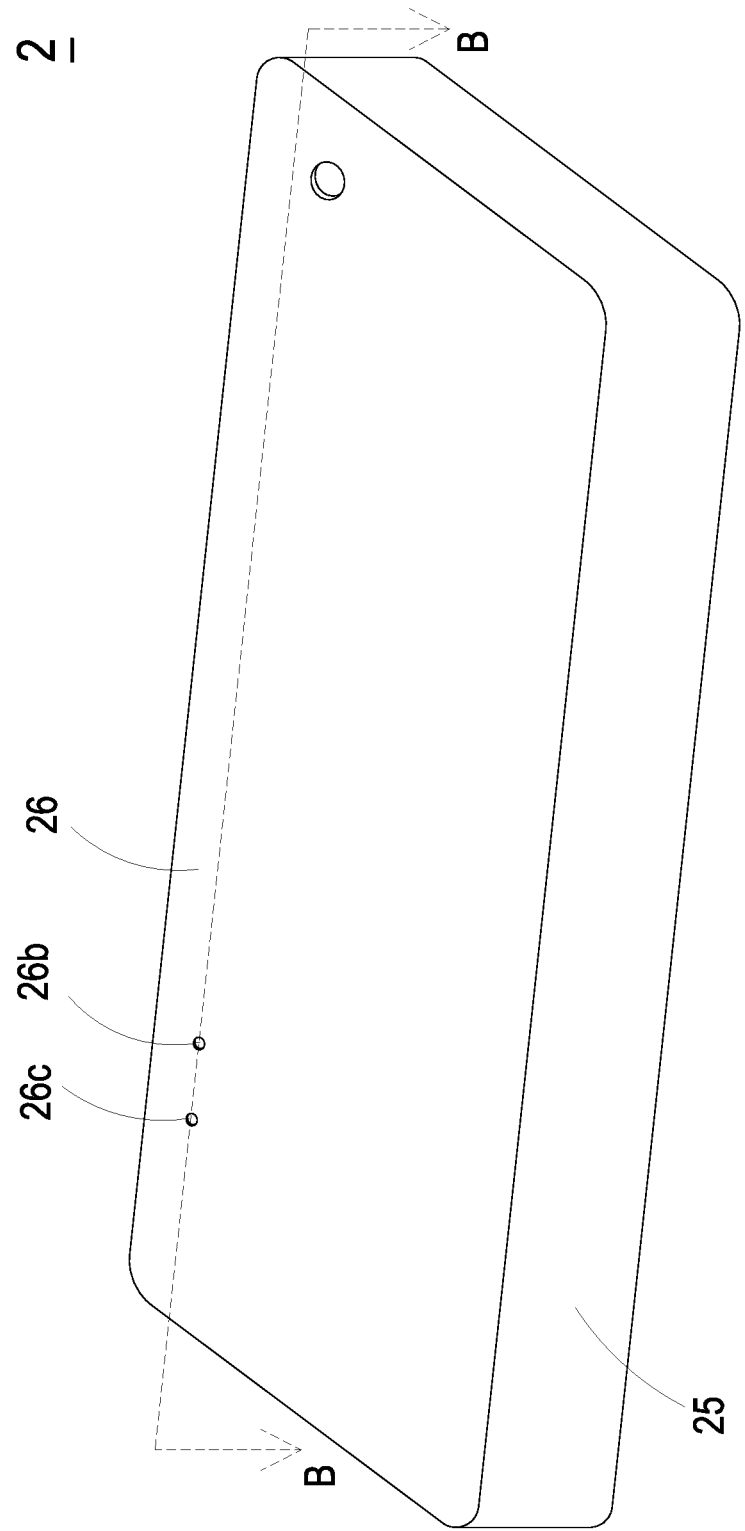
FIG. 6B is a schematic perspective view illustrating the outer appearance of the casing of an electronic device according to the embodiment of the present disclosure and taken along a rear side.

FIG. 6A is a schematic perspective view illustrating the outer appearance of the actuating and sensing apparatus and a casing of an electronic device according to the embodiment of the present disclosure and taken along a front side. FIG. 6B is a schematic perspective view illustrating the outer appearance of the casing of an electronic device according to the embodiment of the present disclosure and taken along a rear side. FIG. 6C is a schematic cross-sectional view illustrating the actuating and sensing apparatus and the casing of the electronic device of FIG. 6A and taken along the line BB. The actuating and sensing apparatus 1 of the present disclosure could be applied in a casing of any portable electronic device. For example, the casing of a notebook computer, a smart phone, a smart watch, a tablet computer or any other appropriate portable electronic devices. In the following description, a casing of the smart phone is exemplified for being detailed illustrated. Please refer to FIGS. 6A to 6C, the casing 2 is for using in a smart phone (not shown). The casing 2 includes a lateral wall 25, a plate 26 and an actuating and sensing apparatus 27. In this embodiment, the actuating and sensing apparatus 27 includes a circuit board 20, a housing 21, an actuating device 22 and a sensor 23. The housing 21 is disposed on the circuit board 20 and includes an entrance opening 212, an exit opening 211 and a compartment 210. The compartment 210 is in communication with an external environment outside the housing 21 through the entrance opening 212 and the exit opening 211. The actuating device 22 is disposed within the compartment 210 and closes the exit opening 211. The sensor 23 is disposed within the compartment 210 and corresponding to the entrance opening 212. In this embodiment, the structures and the operations of actuating and sensing apparatus 27 is the same as that of the previous embodiment and will not be described in details herein. The plate 26 further includes a bottom surface 26a, a first opening 26b and a second opening 26c. The housing 21 of the actuating and sensing apparatus 27 is attached on the bottom surface 26a of the plate 26. The entrance opening 212 is aligned and in communication with the second opening 26c. The exit opening 211 is aligned and in communication with the first opening 26b. In an embodiment, the lateral wall 25 is connected to the plate 26, and an accommodation space 28 is defined therebetween. The actuating and sensing apparatus 27 is disposed within the accommodation space 28. When the actuating device 22 of the actuating and sensing apparatus 27 is enabled, a gas within the compartment 210 is guided to the external environment outside the housing 21 and the casing 2 through the exit opening 211 and the first opening 26b, and a pressure gradient is generated in the compartment 210 of the housing 21 so as to introduce the gas from the external environment outside the casing 2 into the compartment 210 through the second opening 26c and the entrance opening 212 to make the gas monitored by the sensor 23. By assembling the casing 2 with a smart phone or any other portable electronic device, it is convenient for users to carry it around and can immediately acquire the information about the ambient gas everywhere and at any time. When toxic or hazardous gases are detected in ambient air, the smart phone assembled with the casing 2 may suggest the user to take protective measures for preventing from gas explosion, gas poisoning or the like.

Please refer to FIG. 6C again. In this embodiment, the actuating and sensing apparatus 27 of the casing 2 further includes a first protective film 241 and a second protective film 242. The first protective film 241 and the second protective film 242 are respectively close the entrance opening 212 and the exit opening 211. The first protective film 241 and the second protective film 242 are waterproof and dustproof film structures. Moreover, only the gas is allowed to pass through the first protective film 241 and the second protective film 242. Since the first protective film 241 and the second protective film 242 are waterproof and dustproof, the moisture and the dust are prevented from entering the compartment 210 through the entrance opening 212 and the exit opening 211, and the actuating device 22 and the sensor 23 within the compartment 210 are not rusted or damaged. In this embodiment, the first protective film 241 and the second protective film 242 comply with the Rating IP64 of International Protection Marking (IEC 60529), i.e., Dust protection level 6 (Complete protection, No ingress of dust) and Water protection level 4 (Protection against Splashing of water: Water splashing against the enclosure from any direction shall have no harmful effect). In another embodiment, the first protective film 241 and the second protective film 242 comply with the Rating IP68 of International Protection Marking (IEC 60529), i.e., Dust protection level 6 and Water protection level 8 (Continuous immersion in water that it produces no harmful effects).

From the above descriptions, the present disclosure provides the actuating and sensing apparatus. When the piezoelectric actuator is activated, a gas is introduced into the actuating device of the actuating and sensing apparatus, and a pressure gradient is generated in the fluid channels and the chambers of the actuating device to facilitate the gas to flow out at a high speed. The ambient gas is introduced into the compartment of the housing through the entrance opening. Consequently, the gas can be circulated and quickly transferred while achieving silent efficacy. Due to the arrangement of the first protective film and the second protective film, the components within the housing are not rusted or damaged by the moisture or the dust. Consequently, the gas transportation efficiency is enhanced. Since the possibility of causing the damage of the actuating and sensing apparatus is reduced, the performance of transferring and sensing the gas will be enhanced. Moreover, since the overall volume and thickness of the actuating and sensing apparatus are reduced, the actuating and sensing apparatus can be applied to the miniature device or the portable electronic device. By using the portable electronic device of the present disclosure, it is convenient for users to carry it around and can immediately acquire the information about the ambient gas everywhere and at any time. If the concentration or content of a harmful gas in the ambient air exceeds a threshold value, the actuating and sensing module prompts the user that the concentration or content of the harmful gas in the environment is too high. After realizing the harmful level of the ambient gas, the user can escape quickly or take protective measures. Consequently, the possibility of causing the user's coma, poisoning the user or resulting in gas explosion will be largely reduced.

While the invention has been described in terms of what is presently considered to be the most practical and preferred embodiments, it is to be understood that the invention needs not be limited to the disclosed embodiment. On the contrary, it is intended to housing various modifications and similar arrangements included within the spirit and scope of the appended claims which are to be accorded with the broadest interpretation so as to encompass all such modifications and similar structures.

What is claimed is:

1. An actuating and sensing apparatus, comprising:
   a circuit board;
   a housing disposed on the circuit board and comprising an entrance opening, an exit opening and a compartment, wherein the compartment is in communication with an external environment of the housing through the entrance opening and the exit opening;
   an actuating device disposed within the compartment and closing the exit opening correspondingly; and
   a sensor disposed within the compartment and corresponding to the entrance opening;
   wherein when the actuating device is enabled, a gas within the compartment is guided to an external environment outside the housing through the exit opening, and a pressure gradient is generated in the compartment so as to introduce a gas from the external environment outside the housing into the compartment through the entrance opening to make the gas monitored by the sensor.

2. The actuating and sensing apparatus according to claim 1, wherein the actuating and sensing apparatus further comprises a first protective film and a second protective film, the first protective film and the second protective film respectively closing the exit opening and the entrance opening, wherein the first protective film and the second protective film are waterproof and dustproof film structures, and the gas is allowed to pass through the first protective film and the second protective film.

3. The actuating and sensing apparatus according to claim 2, wherein the first protective film and the second protective film comply with Rating IP64 of International Protection Marking (IEC 60529).

4. The actuating and sensing apparatus according to claim 2, wherein the first protective film and the second protective film comply with Rating IP68 of International Protection Marking (IEC 60529).

5. The actuating and sensing apparatus according to claim 1, wherein the sensor is selected from at least one of an oxygen sensor, a carbon monoxide sensor, a carbon dioxide sensor, a temperature sensor, an ozone sensor, a particulate sensor, a sulfur dioxide sensor, a nitrogen dioxide sensor, a volatile organic compound sensor and combinations thereof.

6. The actuating and sensing apparatus according to claim 1, wherein the circuit board has the length of 19.7 mm, the width of 15.8 mm and the height of 0.8 mm, and the housing has the length of 17.8 mm, the width of 14.8 ram and the height of 2.6 mm.

7. The actuating and sensing apparatus according to claim 1, wherein the actuating device comprises:
   a gas inlet plate having at least one inlet;
   a resonance plate; and
   a piezoelectric actuator,
   wherein the gas inlet plate, the resonance plate and the piezoelectric actuator are stacked on each other sequentially, and a gap is formed between the resonance plate and the piezoelectric actuator to define a first chamber, wherein when the piezoelectric actuator is enabled, the gas is fed into the at least one inlet of the gas inlet plate and transferred to the first chamber through the resonance plate, so that the gas is inhaled from the entrance opening.

8. The actuating and sensing apparatus according to claim 7, wherein the gas inlet plate further comprises at least one convergence channel and a central cavity, wherein the at least one convergence channel is aligned with the at least one inlet, and the gas fed into the at least one inlet is guided to the central cavity, wherein the resonance plate has a central aperture corresponding to the central cavity of the gas inlet plate, wherein the piezoelectric actuator has a suspension plate, an outer frame, at least one bracket and a piezoelectric ceramic plate, wherein the bracket is connected between the suspension plate and the outer frame, and the piezoelectric ceramic plate is attached on a surface of the suspension plate.

9. The actuating and sensing apparatus according to claim 7, wherein the actuating device further comprises at least one insulation plate and a conducting plate, wherein the at least one insulation plate and the conducting plate are stacked on each other sequentially and located under the piezoelectric actuator.

10. A casing for using in an electronic device, the casing comprising:
    an actuating and sensing apparatus including a circuit board, a housing, an actuating device and a sensor, wherein the housing is disposed on the circuit board and comprises an entrance opening, an exit opening and a compartment, the compartment is in communication with an external environment outside the housing through the entrance opening and the exit opening, the actuating device is disposed within the compartment and closes the exit opening, and the sensor is disposed within the compartment and corresponding to the entrance opening;
    a plate including a bottom surface, a first opening and a second opening, wherein the housing of the actuating and sensing apparatus is attached on the bottom surface, the entrance opening is aligned and in communication with the second opening, and the exit opening is aligned and in communication with the first opening; and
    a lateral wall connected to the plate;
    wherein when the actuating device of the actuating and sensing apparatus is enabled, a gas within the compartment is guided to an external environment outside the casing through the exit opening and the first opening, and a pressure gradient is generated in the compartment so as to introduce a gas from the external environment outside the casing into the compartment, through the second opening and the entrance opening to make the gas monitored by the sensor.

11. The casing according to claim 10, wherein the actuating and sensing apparatus further comprises a first protective film and a second protective film, the first protective film and the second protective film respectively close the exit opening and the entrance opening, wherein the first protective film and the second protective filth are waterproof and dustproof film structures, and the gas is allowed to pass through the first protective film and the second protective film.

12. An actuating and sensing apparatus, comprising:
at least one circuit board;
at least one housing disposed on the circuit board and comprising at least one entrance opening, at least one exit opening and at least one compartment, wherein the compartment is in communication with an external environment of the housing through the entrance opening and the exit opening;
at least one actuating device disposed within the compartment and closing the exit opening; and
at least one sensor disposed within the compartment and corresponding to the entrance opening;
wherein when the actuating device is enabled, a gas within the compartment is guided to an external environment outside the housing through the exit opening, and a pressure gradient is generated in the compartment so as to introduce a gas from the external environment outside the housing into the compartment through the entrance opening to make the gas monitored by the sensor.

* * * * *